United States Patent [19]

Henkin

[11] Patent Number: 5,384,308
[45] Date of Patent: Jan. 24, 1995

[54] COMPOSITION AND METHOD FOR ENHANCING WOUND HEALING

[76] Inventor: R. I. Henkin, 6601 Broxburn Dr., Bethesda, Md. 20817

[21] Appl. No.: 76,058

[22] Filed: Jun. 14, 1993

[51] Int. Cl.⁶ .................. A61K 37/16; A61K 35/37
[52] U.S. Cl. ............................. 514/8; 514/7; 514/969; 424/550; 530/843
[58] Field of Search .............. 514/2, 938, 969, 7, 514/8; 424/85.8, 550; 530/843

[56] References Cited

U.S. PATENT DOCUMENTS 4,066,405  1/1978  Henkin .................. 436/86

OTHER PUBLICATIONS

Li et al Br. J. Surg. 68:783–743, 1981.

Primary Examiner—Christine M. Nucker
Assistant Examiner—Julie Krsek-Staples
Attorney, Agent, or Firm—Lowe, Price, LeBlanc & Becker

[57] ABSTRACT

There is described herein a wound healing enhancing medicinal composition formulated from the salivary protein Lumicarmine. Lumicarmine is a phosphoglycoprotein with a molecular weight of 34.5 kD. About 80% of the total amino acid residues are proline glycine and glutamic acid and another 10% are lysine and arginine. Lumicarmine stains pink violet after gel electrophoresis and staining with Coomassie Brilliant Blue R-250 dye.

5 Claims, 10 Drawing Sheets

COMPOSITION AND METHOD FOR ENHANCING WOUND HEALING

FIELD OF THE INVENTION

This invention relates to the discovery and isolation of a salivary protein and the use of the same in a medicinal composition to promote healing as well as in the preparation of antibodies which also have medicinal properties. This invention also relates to the preparation of a continuous culture of human parotid cells and modification of the salivary proteins generated in such cultures.

DESCRIPTION OF THE PRIOR ART

In my prior U.S. Pat. No. 4,066,405, which issued Jan. 3, 1978, there was described a method for the total protein fractionization of human saliva and the discovery of a zinc protein therein influential in taste acuity. This protein was named Gustin. In the course of further research, another major protein in saliva has been discovered to have medicinal properties.

It has been an observed phenomenon that in animals wounds heal faster if the animal is permitted to lick the wound, and most efficient healing is promoted by communal licking. In contrast, it is also well known that the mouth and, particularly, the human mouth is an extremely dirty environment. Human bite wounds are typically among the most difficult wounds to treat, for this reason. However, as is also well known, wounds in the mouth heal very quickly, and in many cases without any treatment. Research then has been directed to the characterization of human saliva in an effort to identify a factor therein, if any, responsible for healing.

Several growth factors in saliva have been discovered in recent years including EGF, FGF, TGF alpha and TGF beta, and many felt that these growth factors were responsible for healing. However, isolation, characterization and synthesis of these peptides and their application to wounds showed a wound healing which was enhanced to a slight degree, but healing of chronic lesions was not enhanced at all. This led to the observation that these peptides, albeit minimally effective in accelerating healing of acute wounds, were effective only in the presence of their specific receptors in the wound, and these receptors were identified only in acute, not chronic wounds. In chronic wounds without the presence of specific receptors for these peptides, their effects were negligible. These factors then were not believed to be responsible for healing of wounds in animals promoted by licking.

In order to evaluate the healing properties of salivary proteins identified in the above United States patent and related research, it was necessary to characterize the mechanisms involved in the complex process of healing wounds. Wound healing involves multiple steps and the interaction of multiple body systems. There are then four major components of the wound healing mechanism as follows:

I. Initial inflammatory events include neutrophil accumulation or infiltration associated with loss of endothelial cells, increased vascular permeability and degradation of vascular basement membranes. Several permeability factors may play roles in this aspect of the process including prostaglandins, various peptides, complement factors, cytokines, and platelet activating factor. These initial processes continue only for a short time period of, for example, 6 to 24 hours.

II. These steps are followed by influx of monocytes into the lesion with subsequent monocyte maturation into mature, active macrophages with removal of cells and cellular debris.

III. These steps are followed by simultaneous stimulation of fibroblast division, collagen formation and fibrosis with IV. subsequent stimulation of epithelial cell division with regeneration of normal cellular structures and functions.

SUMMARY OF THE INVENTION

A protein, however, a major constituent of human saliva, has been identified as the wound healing factor in saliva and a medicinal composition containing an effective amount of the same has been proven to be effective in promoting healing. In addition, antibodies to this protein have been developed for additional medicinal uses, as will be subsequently described.

The protein of this invention, it is believed, is involved in the healing process, and forms a matrix upon which later physiological events and processes take place. The action of the protein then does not require a receptor in order for its action to be effective. Since this protein contains as part of its primary structure some of the primary structural elements of a very primitive form of collagen, the major constituent of skin or connective tissue, it appears to interact with the wound forming a structural foundation which allows initiation of the healing process. The protein, albeit not a collagen molecule per se, appears to be involved in several steps in early wound healing: (1) in the formation of the basal membrane upon which the healing process takes place, (2) in enhancing vascular basement membrane permeability, and (3) in supplying stability to the wound milieu thereby enhancing subsequent steps in the complex healing process. However, because of other structural characteristics, it may also assist healing in several later stages of the process, too.

The protein identified herein has been named Lumicarmine. It has been found to be a phosphoglycoprotein of 34.5 kD. It contains 6 moles of phosphate per mole of protein and 39% carbohydrate. The amino acid and sugar composition of the protein are shown in Table I. The amino acid and sugar composition of other forms of this protein are shown in Table II.

TABLE I

| AMINO ACID AND CARBOHYDRATE COMPOSITION OF LUMICARMINE FROM CM-CELLULOSE ||
| --- | --- |
| | Fraction 1 residues per 1000 |
| Amino acids | |
| Lysine | 43 |
| Histidine | 11 |
| Arginine | 37 |
| Asparagine | 50 |
| Threonine | 12 |
| Serine | 48 |
| Glutamine | 180 |
| Proline | 327 |
| Glycine | 224 |
| Alanine | 16 |
| Half Cysteine | 0 |
| Valine | 0 |
| Methionine | 0 |
| Isoleucine | 3 |
| Leucine | 8 |

TABLE I-continued
AMINO ACID AND CARBOHYDRATE COMPOSITION OF LUMICARMINE FROM CM-CELLULOSE

| | Fraction 1 residues per 1000 |
|---|---|
| Xα | 0 |
| Tryptophanβ | 0 |
| Phenylaline | 0 |
| Tyrosine | 0 |
| Hydroxyproline | 0 |
| | % g/100 g |
| Sialic acid | 2.80 |
| | % g/100 g |
| Neutral sugars | 39.3 |
| | relative amounts, % |
| Carbohydrates | |
| Mannose | 1.00 |
| Fucose | 1.72 |
| Galactose | 1.62 |
| N-Acetylglucosamine | 5.02 |

αX, unknown substance appearing after leucine.
βEstimated from A280 and from tyrosine content as determined from the amino acid analysis using molar extinction coefficient values of 5500 and 1200 for tryptophanyl and tyrosyl absorbance at A280, respectively.

TABLE II
AMINO ACID AND CARBOHYDRATE COMPOSITION OF THREE OTHER FORMS OF LUMICARMINE FROM CM-CELLULOSE

| | Fractions | | |
|---|---|---|---|
| | 2 | 3 | 4 |
| | residues per 1000 | | |
| Amino acids | | | |
| Lysine | 42 | 45 | 46 |
| Histidine | 10 | 10 | 12 |
| Arginine | 36 | 37 | 44 |
| Asparagine | 54 | 47 | 44 |
| Threonine | 5 | 6 | 6 |
| Serine | 37 | 35 | 29 |
| Glutamine | 187 | 179 | 194 |
| Proline | 357 | 381 | 389 |
| Glycine | 225 | 229 | 206 |
| Alanine | 0 | 4 | 6 |
| Half Cysteine | 0 | 0 | 0 |
| Valine | 0 | 0 | 0 |
| Methionine | 0 | 0 | 0 |
| Isoleucine | 0 | 1 | 0 |
| Leucine | 0 | 3 | 4 |
| Xα | 49 | 41 | 20 |
| Tryptophanβ | 0 | 0 | 0 |
| Phenylalanine | 0 | 0 | 0 |
| Tyrosine | 0 | 0 | 0 |
| Hydroxyproline | 0 | 0 | 0 |
| | % g/100 g | | |
| Sialic acid | 1.32 | 1.02 | 0.74 |
| | % g/100 g | | |
| Neutral sugars | 30.7 | 25.0 | 20.2 |
| | relative amounts, % | | |
| Carbohydrates | | | |
| Mannose | 1.00 | 1.00 | 1.00 |
| Fucose | 1.69 | 1.13 | 1.00 |
| Galactose | 1.20 | 1.08 | 0.92 |
| N-Acetylglucosamine | 4.18 | 4.05 | 4.41 |

αX, unknown substance appearing after leucine
βEstimated from A280 and from tyrosine content as determined from the amino acid analysis using molar extinction coefficient values of 5500 and 1200 for tryptophanyl and tyrosyl absorbance at A280, respectively.

Lumicarmine is not a typical protein in that six of the amino acids normally present in proteins are absent and four others are present in concentrations below 1%. In addition, an unknown compound was found which was present in a concentration of 5% and migrated between leucine and tyrosine. The principal amino acid was proline (33%) and proline, glycine, and glutamic acid comprised about 80% of the total protein on a residue basis. Thus, this protein is unique because it is essentially devoid of aromatic amino acids; it is composed of 80% of pro-gly-glx; it is comprised of 10% lys-arg; it stains pink violet after gel electrophoresis and staining with Coomassie Brilliant Blue R-250 and it contains 6 moles of phosphate per mole of protein. The name Lumicarmine is derived from the high content of phosphorous and its pink violet staining characteristics.

Lumicarmine was initially identified from human parotid saliva which was collected from humans using well recognized techniques such as described in my above-identified patent, U.S. Pat. No. 4,066,405, the disclosure of which is hereby incorporated by reference.

Saliva was then centrifuged at 3000×g for 10 minutes to remove membrane fragments. Saliva was then concentrated on an Amicon concentrator and the concentrate placed onto a Sephacryl S-200 column operated with a 0.01M sodium phosphate buffer at pH 6.8. Lumicarmine was found in fractions II–V of the column. For the purposes of these studies, Lumicarmine only in the fraction in which it was distributed in its highest concentration, i.e., fraction II was used. However, other forms of Lumicarmine are present and differ little from the Lumicarmine in fraction II. These other forms of Lumicarmine also possess wound healing enhancement properties. Lumicarmine in fraction II is approximately 90% homogeneous, with other proteins, including a small amount of Gustin also found.

To purify Lumicarmine further, all protein from fraction II was treated with 0.5M dithiothreitol (DTT) overnight, then dialyzed against 0.01M sodium phosphate, pH 6.8, and placed on a DEAE-A50 Sephadex column operated with 0.01M sodium phosphate, followed by a NaCL gradient, 0.0–0.5M of 200 ml. Early eluates from this column, tubes 4–10 were concentrated, dialyzed against 5 mM sodium phosphate, pH 5.9, placed on a CM-cellulose column and operated with 5 mM sodium phosphate, pH 5.9. The elute from this column yields Lumicarmine which is essentially homogeneous except for small differences in some amino acid and sugar moieties.

Lumicarmine purified to homogeneity was combined with Freund's Adjuvant and injected subcutaneously into the hind leg of a rabbit over a period of four to six weeks and antibodies to the protein were produced and identified by standard antibody dilution techniques.

Also, tissue from a human parotid gland was obtained during surgical removal of a parotid tumor, and that portion identified as normal salivary tissue by light microscopic examination after fixing in 10% formalin and staining with hematoxylin-eosin, was planted in tissue culture dishes in a defined medium. Cell growth was achieved along with growth of ducts, which is vital to the ability to transplant functional cells into humans. Because there are no lymphocytes in this pure culture of salivary gland cells, this should be transplantable without any adverse immune reaction. After optimal growth was obtained, cells were maintained in a serum-free medium and Lumicarmine was measured by radioimmunoassay in the medium in which the cells were grown. Antibodies to Lumicarmine at the concentration of 1:1000 were placed into the cell culture such that secretion of Lumicarmine was effectively blocked. An antigen-antibody reaction was observed by phase microscopy of the cultured salivary gland cells.

Since Lumicarmine is a protein identified to enhance the speed of healing of wounds, identification and characterization of one or several of the molecular components by which this mechanism operates with subsequent inhibition of its effect on normal healing characterizes a substance which inhibits fibrosis. Thus, when placed in a lesion in which fibrosis is not a preferred result, it can produce the desired effect of inhibiting this healing characteristic. This substance is identified as Antilumicarmine, a modified version of the Lumicarmine protein. Lesions of this type comprise diseases such as progressive systemic sclerosis, morphea, familial cutaneous collagenoma, connective tissue nevi of the collagen type, hyprotrophic scars, keloids, bronchopulmonary dysplasia, sarcoidosis and restenosis and myointimal hyperplasia after vascular angioplasty and vascular surgery.

As noted above, the simultaneous third and fourth stages of inflammation involve the formation and laying down of collagen in a wound or lesion. This process has been defined in a series of complex, yet specific, steps. Upon receiving the message that collagen is required, the genetic information is transferred to precursor forms of collagen in RNAs that are processed to functional mRNA coding for preprocollagen polypeptides. After translation of the procollagen mRNA, newly synthesized polypeptides, the pro-alpha chains undergo extensive post-transitional modifications. Many of these reactions are characterized by specific enzymes with specific cofactors and substrate requirements. Intracellular post-transitional modification includes synthesis of 3-hydroxyproline, 4-hydroxyproline, and hydroxyglysine, glycosylation of hydroxglysines to form galactosyl-0-hydroxylysine and glucosylgalcyosyl-0-hydroglysine residues, mannosylation of the extension peptides, formation of interchange disulfide bonds, and folding of polypeptides into a triple helical confirmation. After secretion of procollagen molecules into the extracellular space, precursor-specific extensions are removed by procollagen N-proteins and procollagen C-proteins, respectively. Collagen molecules then spontaneously align to form a fiber structure that is stabilized by formation of lysine and hydroxylysine-derived crosslinks. Inhibition of any these critical steps could arrest accumulation of collagen.

Since Lumicarmine enhances wound healing, antilumicarmine can interfere with one or several of these steps to inhibit collagen formation and fibrosis. Mechanisms to alter the action of Lumicarmine are multiple: (1) dephosphorylation of Lumicarmine results in induction of an inhibitory form of the molecule; (2) removal of some of the glycoside side chains or the terminal saccharides from some of the glycoside linkages can alter the action of the protein; treatment with mannosidase, fructosidase or galactosidase can inactivate wound healing properties of protein and induce an antihealing effect.

Similarly, Antilumicarmine may also act as an antitumor promoter or anticancer agent since it can act as an inhibitor of those properties which promote chronic inflammation and thereby inhibit growth and spread of tumors.

The invention then includes the identification of Lumicarmine, the preparation thereof, and the use to promote healing as well as the use thereof to develop Antilumicarmine and its medicinal use as an inhibitor of fibrosis or other healing properties.

Accordingly, it is an object of this invention to identify a protein from human saliva which is responsible for promoting healing of wounds.

It is yet another object of this invention to identify a protein from human saliva and use the same in a medicinal composition to promote healing.

It is another object of this invention to provide a salivary protein, Lumicarmine, in a medicinal form for topical application to promote the healing of wounds and other lesions.

It is still another object of this invention to provide Antilumicarmine derived from Lumicarmine and which is useful in interrupting or disrupting the normal body healing process.

It is still another object of this invention to provide antibodies to Lumicarmine which will block secretion of Lumicarmine in salivary glands.

It is still another object of this invention to provide a medicinal composition derived from the human salivary protein Lumicarmine which can be applied to wounds and similar lesions topically for therapeutic results.

It is yet another object of this invention to provide a continuous culture of human parotid cells for transplanting into humans to treat diseases of salivary lack or abnormality or for generating salivary proteins.

These and other objects will become readily apparent with reference to the drawings and following description wherein:

DETAILED DESCRIPTION OF THE INVENTION

Figure 1:
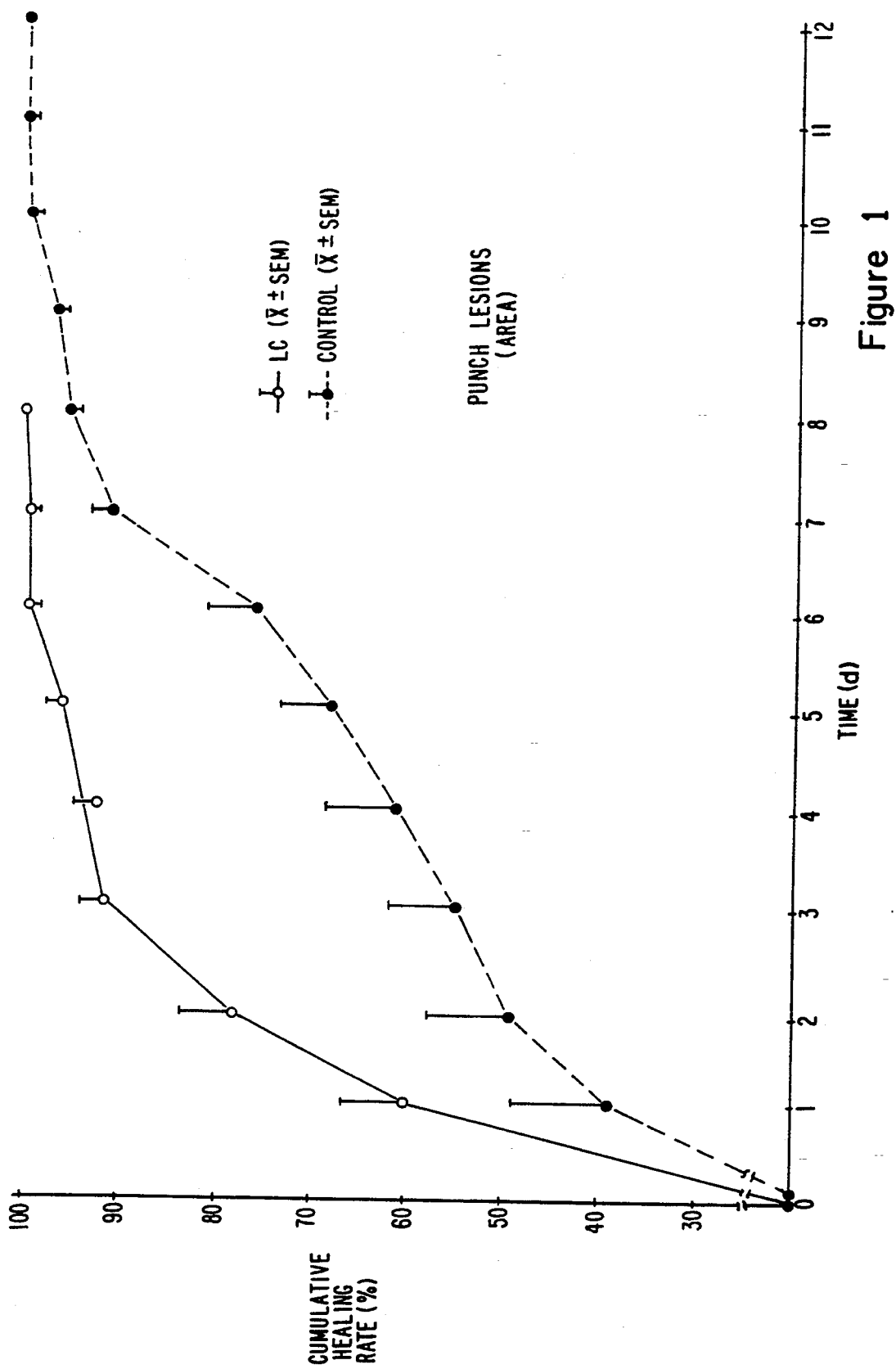
FIG. 1 is a graph depicting the cumulative healing rate versus time for punch biopsy lesions treated with Lumicarmine in an emollient vehicle and emollient vehicle treated controls.

In order to evaluate the effectiveness of Lumicarmine against wounds, the following procedures were utilized.

Animal Tests

Eight Sprague-Dawley rats approximately 250 g in weight were housed individually in stainless steel cages for six days prior to the study and for each day after the study was begun. Animals were given access to rat chow and tap water ad libitum throughout the study.

On Day 7 the rats were anesthetized with ketamine, 0.01 mg/kg given intraperitonealy and the hair over their dorsal surface from the level of the thorax to the tail shaved down to the dermis with an electric razor. The animals were then divided into three groups. Two groups, labeled A and B, consisted of three rats each and one group, labeled C, consisted of two rats. Elizabethan collars were placed on each rat such that none could reach their dorsal surface with their mouth.

For groups A and B sets of lesions were made in each flank of each rat. On the left flank, three 3 mm circular punch biopsies of skin down to the fascia cover the psoas and paraspinal muscles were obtained with a Hayes-Martin punch biopsy instrument, the skin removed after undermining with an iris scissors. On the right flank two longitudinal incisions, approximately 1.5 cm in length, were made with a scalpel blade, the lesion extending down to the fascia of the psoas and paraspinal muscles. These lesions were not closed with sutures but the edges were approximated manually such that closure by semiprimary intent was obtained. Hemostasis of all lesions was obtained by pressure with clean but not sterile 2×2 cotton gauze piedgets. By these techniques two types of lesions were obtained (1) three circular punch lesions in each rat which would close by secondary intention and (2) two incision lesions in each rat which would close by semiprimary intention.

To the other two rats a circular area of skin of approximately 3 mm diameter was excised from the mid dorsal region with an iris scissors down to the fascia of the paraspinal muscles. Hemostasis of each single lesion was obtained by pressure with 2×2 cotton gauze pads.

Each rat was then placed on a light box while anesthetized and under standard conditions of illumination, distance, film, exposure, film speed and photographic lens opening a photograph was obtained. Subsequent to each photograph, each of the five lesions in each rat in group A was covered with approximately 0.5 ml of an emulsion labeled A by a stainless steel spatula and each of the 5 lesions on each rat in group B was covered with approximately 0.5 ml of an emulsion labeled B. No treatment was given to the lesions of rats in group C.

All applications and photographs were made by an investigator who was unaware of the identity of the contents of emulsions A or B which, by visual means, appeared identical.

After surgery, lesions in each animal were covered at approximate 12 hour intervals with emulsion A or B. Each day at 4:00–6:00 p.m., prior to the second daily covering, each rat was anesthetized with ketamine, as previously described, and (1) an individual photograph was taken and (2) a photograph of each set of rats given A or B was taken, i.e., A1 B1, A2 B2, A3 B3.

Rats in Group C were also anesthetized and photographed on a regular basis but no treatment was afforded their lesions, as noted earlier.

Chemical Application

Emulsions A and B were applied to lesions on rats in Groups A and B, respectively, without knowledge of the contents of either solution by the investigator applying the solutions.

Emulsion A contained an emollient, E-cream, Nature's Bounty, Inc., Bohemia, N.Y. 11716, comprised of the following: In 1g emulsion was 10 IU vitamin E, water, petrolatum, C12-15 alcohols, benzoate, cetearyl alcohol and ceteareth-20; glyceryl stearate, stearic acid, cetyl esters, mineral oil, sodium magnesium silicate, polysorbate 80, triethanolamine, imidazolidinyl urea, wheat germ oil, methylparaben, propylparaben and BHA. To each gram of this emollient was added 1 ml Lumicarmine, 45 mg/g in 0.01M sodium phosphate.

Emulsion B contained emollient and to each g was added 1 ml 0.01M sodium phosphate, pH 6.8 in place of Lumicarmine.

Emulsions of approximately 4 ml were prepared every two days and applied twice daily, as noted above. Emulsions were refrigerated after use. No emulsions separated upon standing. Emulsions A and B were visually and tactually identical and could not be distinguished except by label.

Measurements

Following development of all photographs and completion of the experiment, diameters of punch lesions and length and width of the linear lesions were measured from each photography by use of an automatic caliper. All measurements were made in duplicate and the mean of each reading recorded. Diameters were used to calculate area and circumference of all circular lesions by standard formulae. Length and width for linear lesions were measured and area calculated. Initial measurements made on Day 1 of the study were used as a baseline and all subsequent measurements were referred to these measurements. Measurements of area and circumference of circular lesions and area of linear lesions were expressed in two ways: (1) cumulative rate of change (i.e., closure or healing) in terms of daily (%) change in area until complete healing was obtained or circumference on a similar cumulative basis until the lesions were completely healed or (2) daily rate of change with respect to the % of the lesion healed per day until the lesions were completely healed. Data for all circular and linear lesions for all animals in each group were combined and mean ±SEM of cumulative and daily rate of change determined.

Data for the two rats in whom lesions were not treated were considered as having circular lesions, the diameter measured, area and circumference calculated and means for each measurement determined. Data were compared to lesion size on Day 1 of the study and cumulative and daily rate of change determined.

Results

Punch Lesions

Area

Data for cumulative change in punch lesion area for animals in Groups A and B are shown in FIG. 1. A significant enhancement in diminution in lesion area in A with respect to B was observed at the first measurement made 24 hours after lesioning (p<0.001). At the first measurement 61% of the lesions were healed in Group A whereas only 39% were healed in Group B.

This acceleration of healing among the Lumicarmine treated rats persisted throughout the study. Lumicarmine treated rats were 92% healed by day 4 whereas it required 7 days for control animals to reach 91% healing. By day 11 area lesions in all rats were essentially closed.

Figure 2:
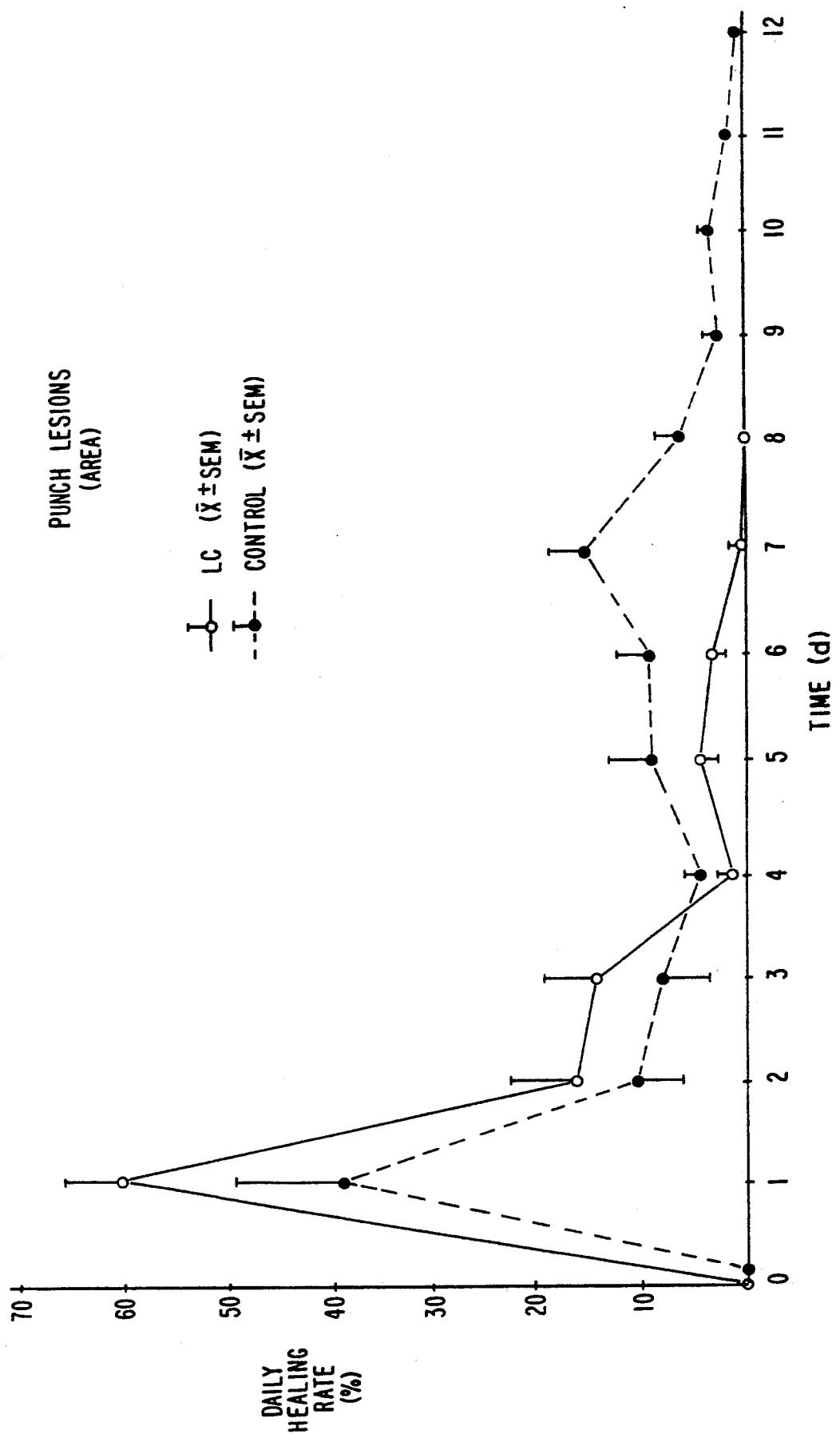
FIG. 2 is a graph depicting the daily healing rate versus time for punch biopsy lesions treated with Lumicarmine in an emollient vehicle and vehicle treated controls.

Data for daily change in punch lesion area for all animals in Groups A and B are shown in FIG. 2. Data analysis illustrates that in Lumicarmine treated rats there is a two phase healing process occurring with the initial phase lasting 4 days during which 92% of the healing process occurred and the second phase lasting 3 days during which time the remaining 8% of the healing process occurred. In the emollient alone treated rats the same two initial processes appear at similar time periods except that at the completion of the first process, i.e., Day 4, 61% of healing had taken place and at the completion of the second, i.e., by Day 7, only 91% of the healing had taken place. For the emollient treated rats an additional third phase appeared to occur which lasted 5 additional days over which the remaining 9% of the healing process occurred.

Circumference

Figure 3:
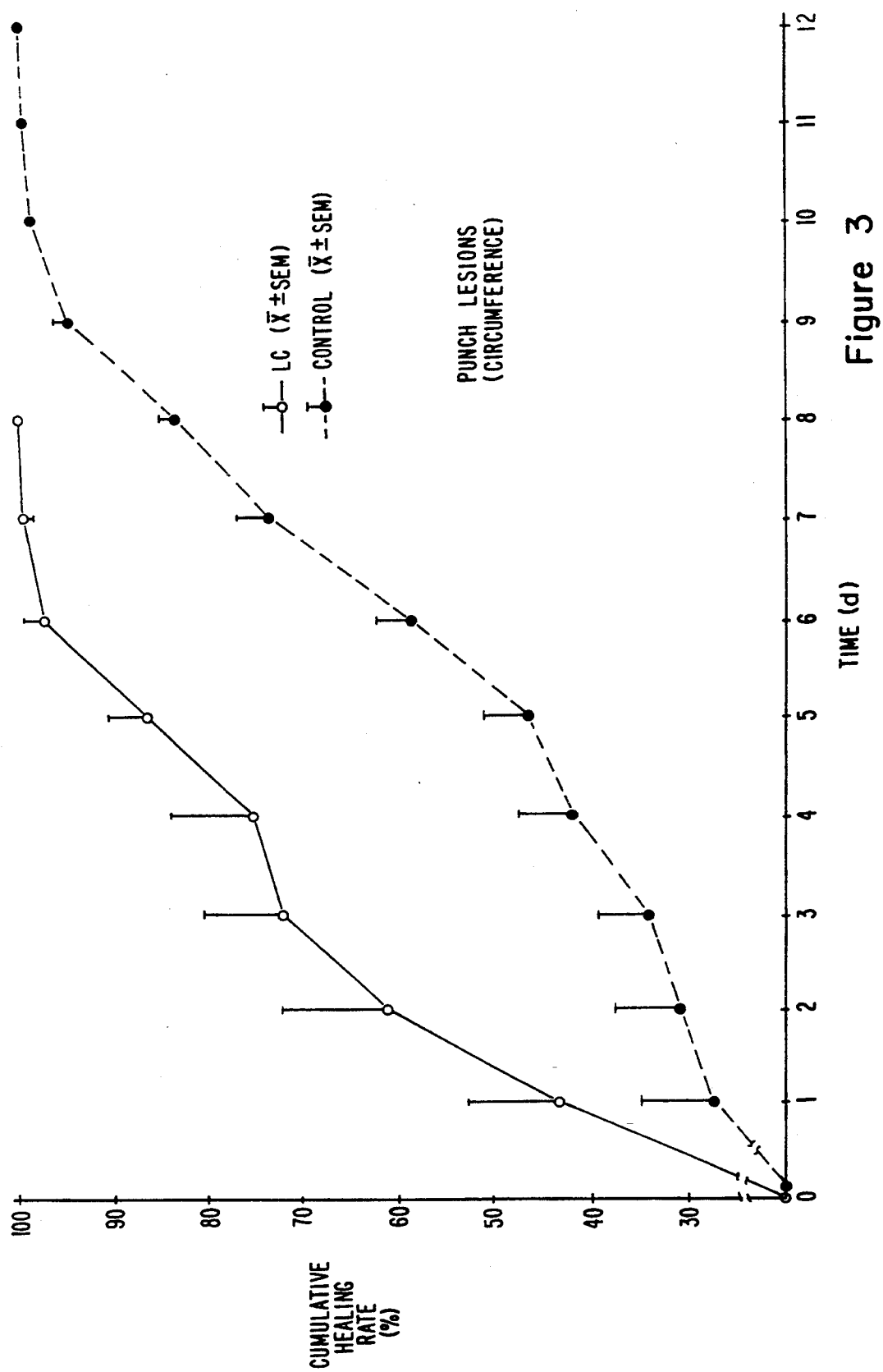
FIG. 3 is a graph depicting the cumulative healing rate against time for the circumference of punch biopsy lesions treated with Lumicarmine in an emollient vehicle and vehicle treated controls.
Figure 4:
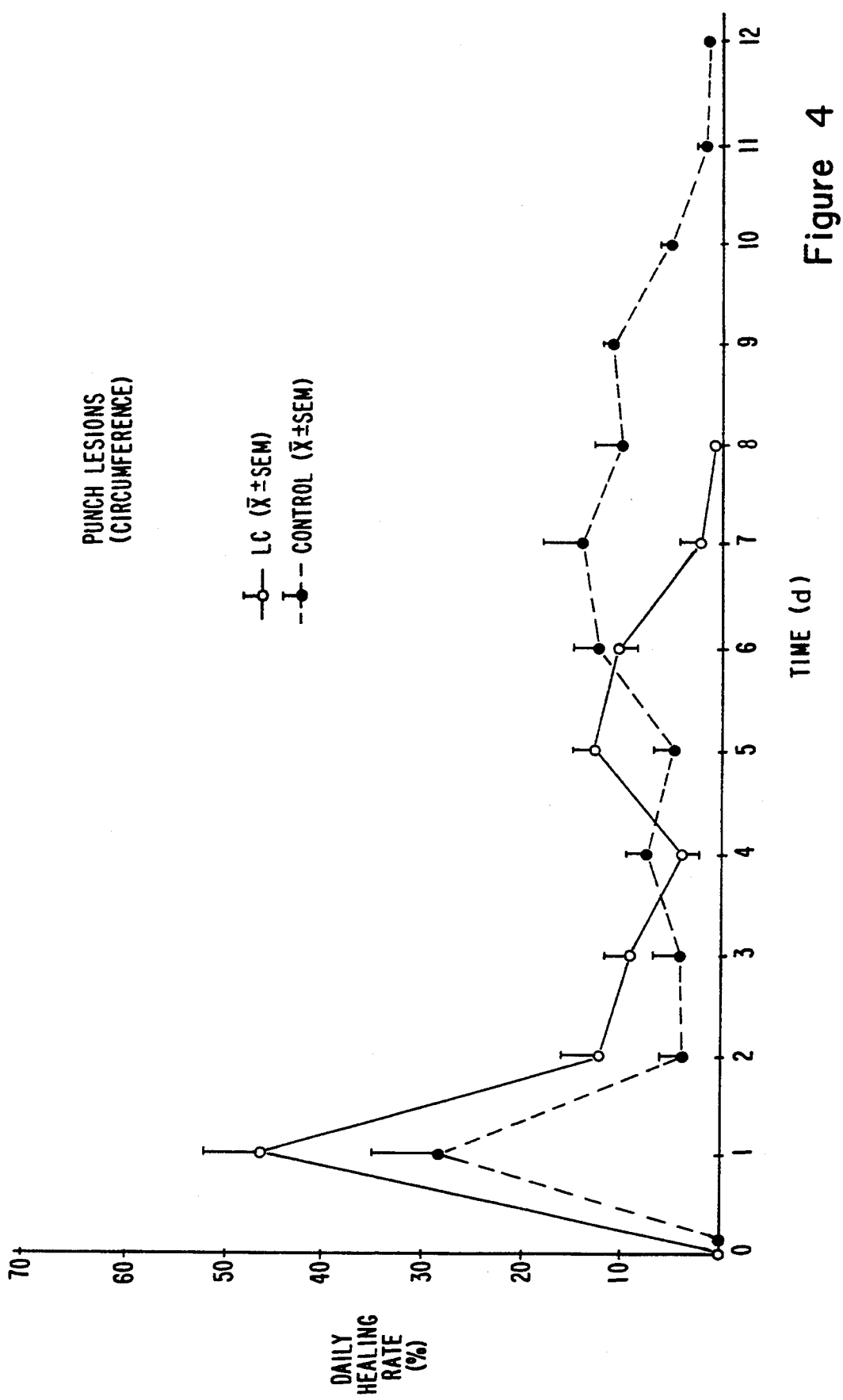
FIG. 4 is a graph depicting the daily rate of change in percent of healing of the circumference of punch biopsy lesions over time for treatment with Lumicarmine in an emollient vehicle and vehicle treated controls.

As with area, a significant enhancement in diminution ($p < 0.001$) in wound circumference was observed in the Lumicarmine treated rats on the first day of treatment compared to changes in the emollient alone treated rats. The magnitude of this difference increased over the first six days of the study with 97% of the circumference diminished at this time in the Lumicarmine treated rats whereas only 58% of the circumference diminished in the emollient treated rats (FIG. 3). Lesions were totally healed by Day 11 in all rats.

When data were analyzed for daily change the two phase pattern of healing observed in area changes in the Lumicarmine treated rats was again observed with phase 1 lasting 4 days and phase 2 lasting an additional 4 days. Among the emollient alone treated rats a four phase pattern of healing was delineated although the timing was not clear cut. Phase 1 extended over 2 days, phase 2 over 3 days, phase 3 over 5 days and phase 4 over 3 days. At the end of phase 1 in the Lumicarmine treated rats 71% of the healing was completed whereas at the end of phase 1 in the emollient treated rats only 31% of the healing was completed. Similarly, at the end of phase 2 in Lumicarmine treated rats 100% of the healing was completed whereas at the end of phase 2, in emollient treated rats only 46% of the healing was completed. All healing was completed by Day 12 but complete healing in emollient treated rats lagged Lumicarmine treated rats by 4 days.

Incision Lesions

Figure 5:
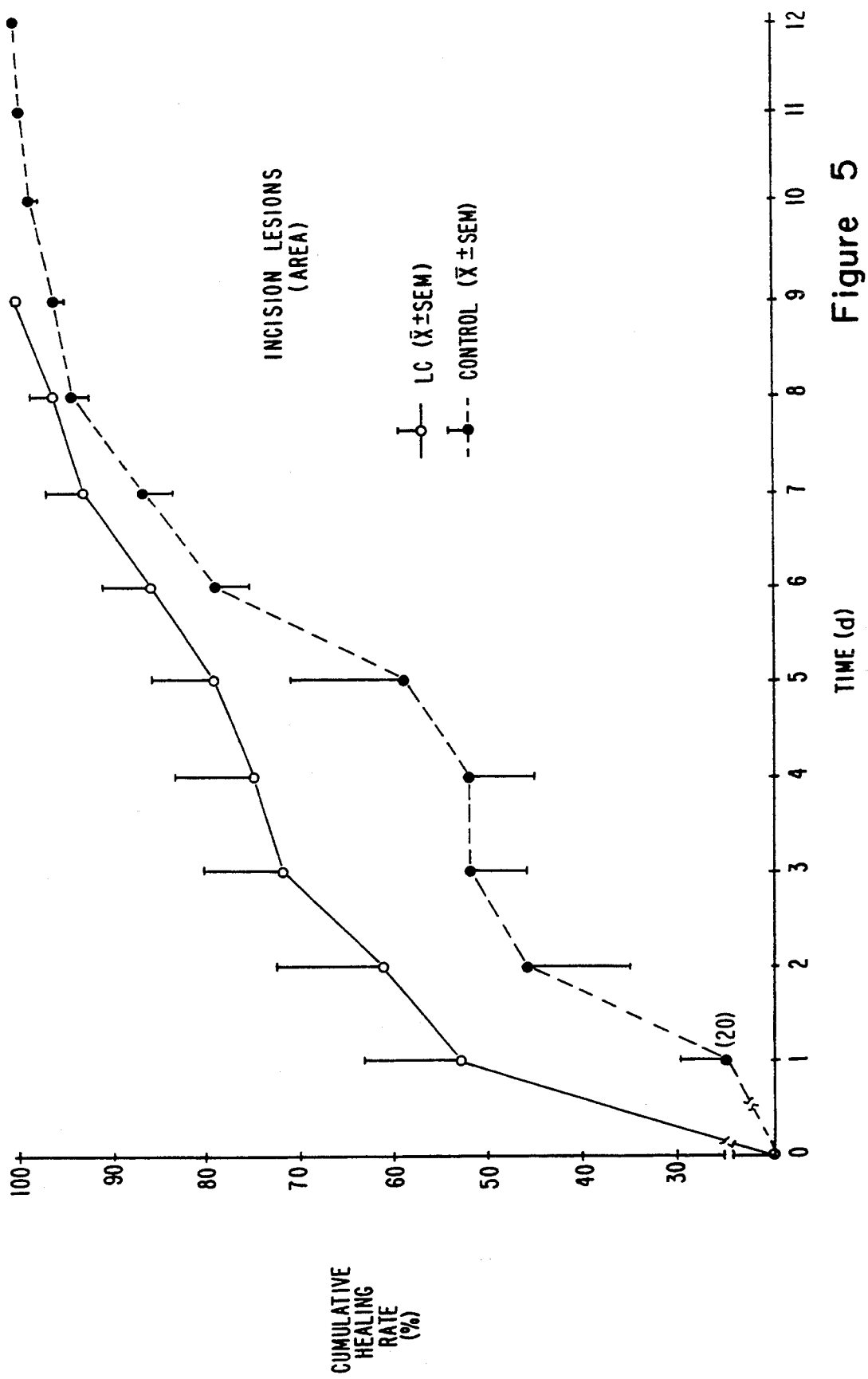
FIG. 5 is a graph depicting the cumulative healing rate of area lesions against time for treatment with Lumicarmine in an emollient vehicle and vehicle treated controls.

Data for cumulative change in incision lesions illustrate that by the end of Day 1 lesions in Lumicarmine treated rats were 53% healed which is significantly greater ($p < 0.001$) than the 20% measured in the emollient treated control rats (FIG. 5). This pattern of healing continued throughout the course of the study with 79% of healing completed in Lumicarmine treated rats by Day 5 whereas only 59% of healing was completed at this time in emollient treated control rats. After Day 6 both groups of rats exhibited similar healing rates with the Lumicarmine treated rats exhibiting complete healing by Day 9 whereas this stage was not achieved by the emollient treated control rats until Day 11.

Figure 6:
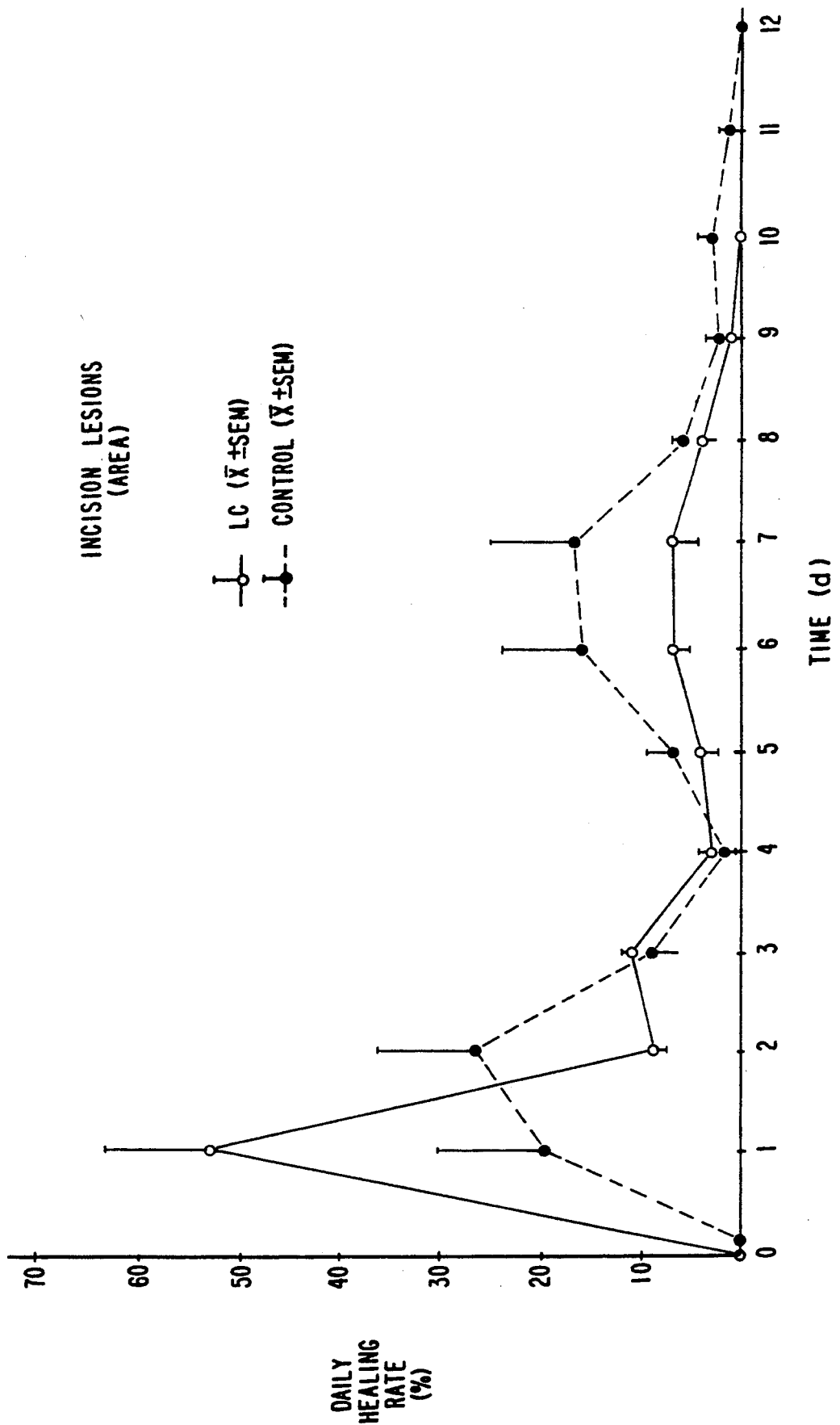
FIG. 6 is a graph depicting the daily rate of change of healing of area lesions over time for treatment with Lumicarmine in an emollient vehicle and vehicle treated controls.

When these data are expressed as rate of daily change (FIG. 6) the pattern of two phase change previously observed following analysis of the punch lesions of Lumicarmine treated rats was also observed in Lumicarmine treated rats with incision lesions. Phase 1 ended at Day 4, phase 2 extended to Day 10. With emollient treated control rats the phases extended over similar time periods with a clear cut delay of 24 hours in phase 1 and an apparent catch up in the rate of healing observed in phase 2; a third phase began at Day 9 and extended to the completion of healing on Day 12.

Control Animals Without Treatment

Figure 7:
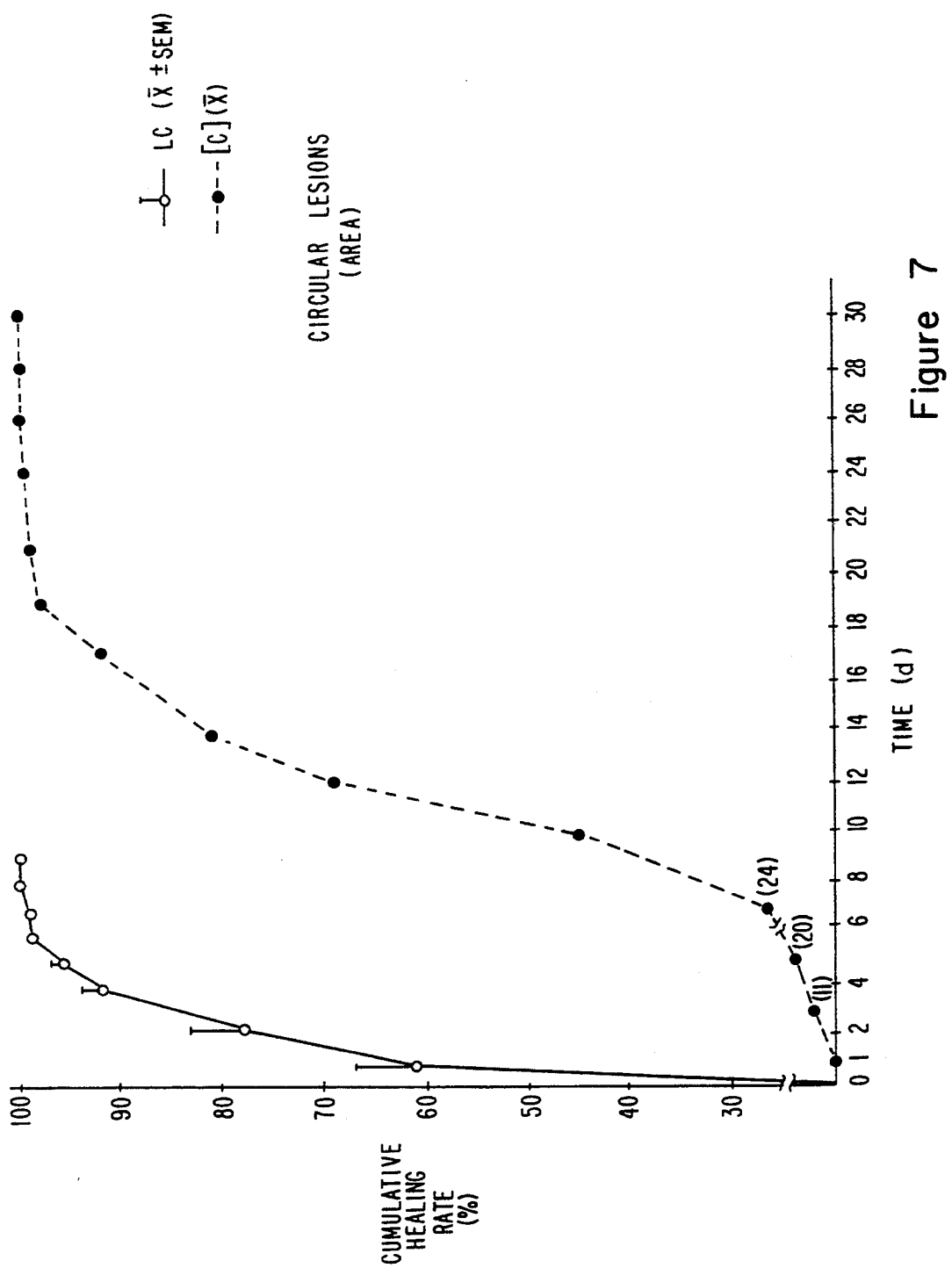
FIG. 7 is a graph comparing progression of cumulative healing of punch biopsy lesions treated with lumicarmine in an emollient vehicle over time with the healing of area of circular biopsy lesions in controls without any treatment over time.

Comparison of cumulative rate of change of area of lesions among Lumicarmine treated rats and those rats who did not receive emollient (wild type lesions) indicate that lesions in control rats required 30 days to heal fully whereas Lumicarmine treated rats healed after 8 days (FIG. 7). Thus control rats required more than three times as long as did Lumicarmine treated rats to heal their wounds completely.

Figure 8:
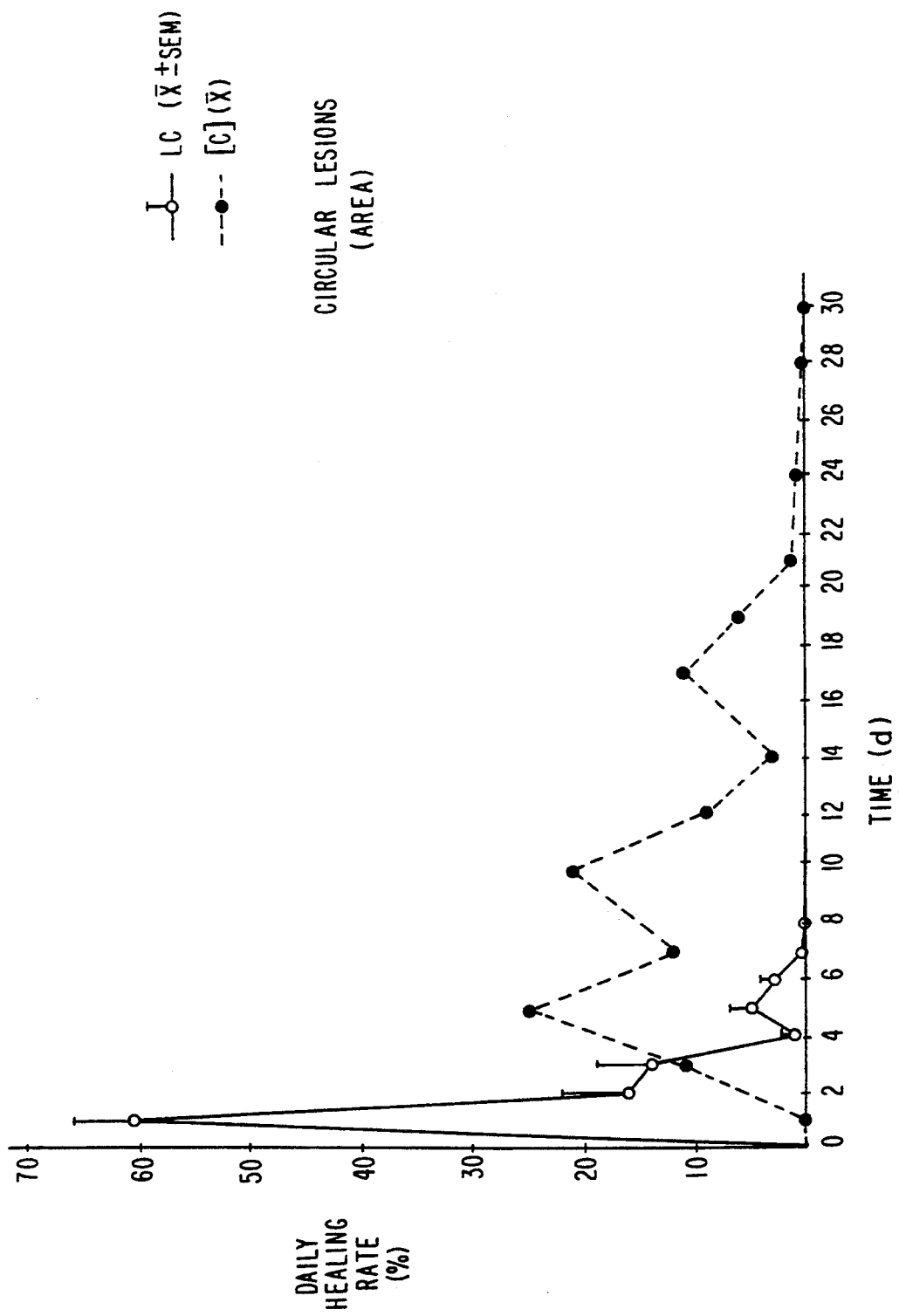
FIG. 8 is a comparison of the daily rate of change of healing of area of punch biopsy lesions treated with Lumicarmine in an emollient vehicle and of circular biopsy lesions in controls without any treatment over time.

Expressed as a daily rate of change the two phase pattern of healing previously observed in Lumicarmine treated rats was again observed whereas a definable four phase pattern of healing was observed (FIG. 8) in lesions of untreated controls, the first phase lasting 7 days, phase 2 lasting 7 days, phase 3 lasting 7 days and phase 4 lasting 9 days before healing was completed.

Figure 9:
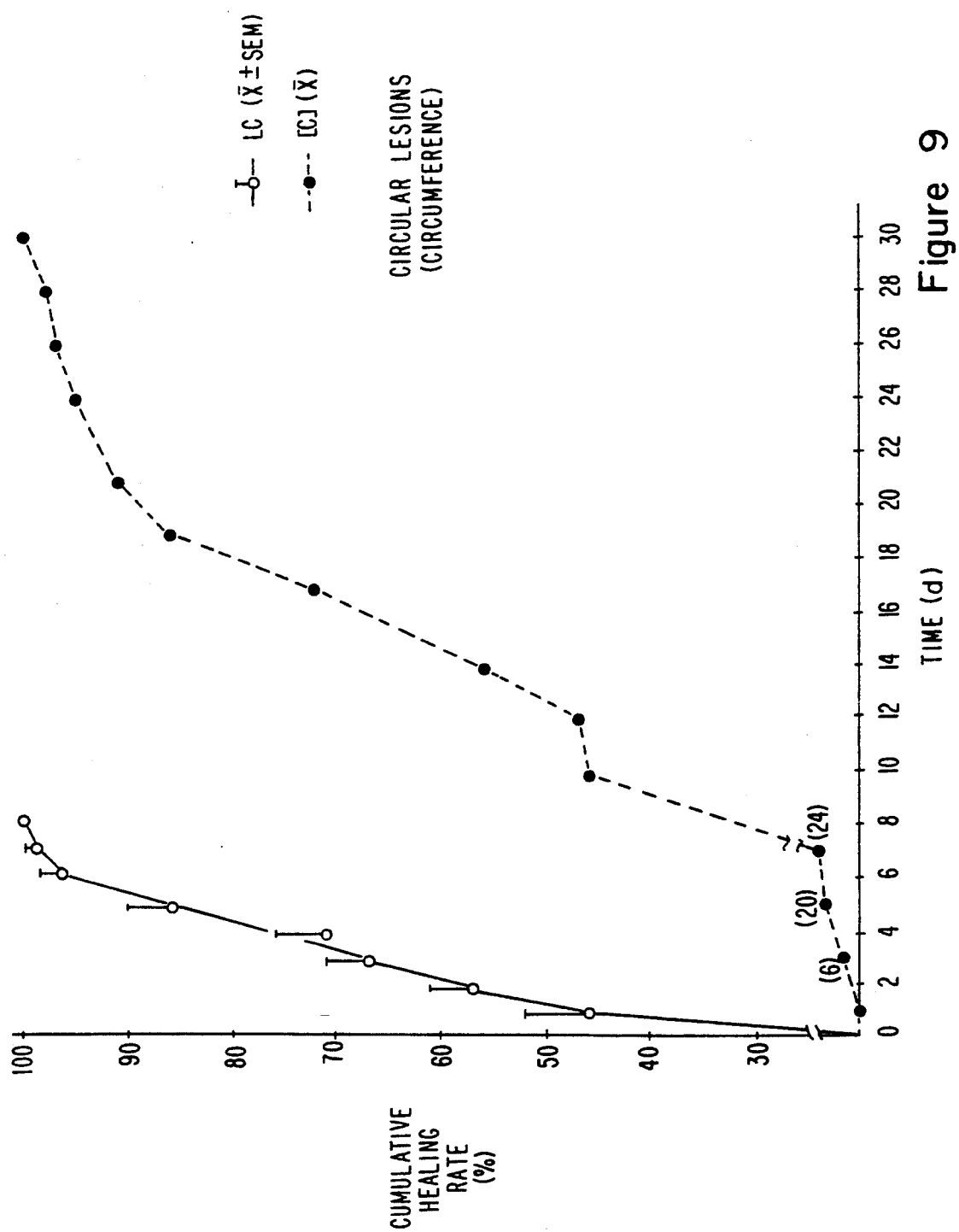
FIG. 9 is a graph depicting the cumulative healing rate against time for the healing of the circumference of punch biopsy lesions treated with Lumicarmine in an emollient vehicle and circular biopsy lesions in controls without any treatment.
Figure 10:
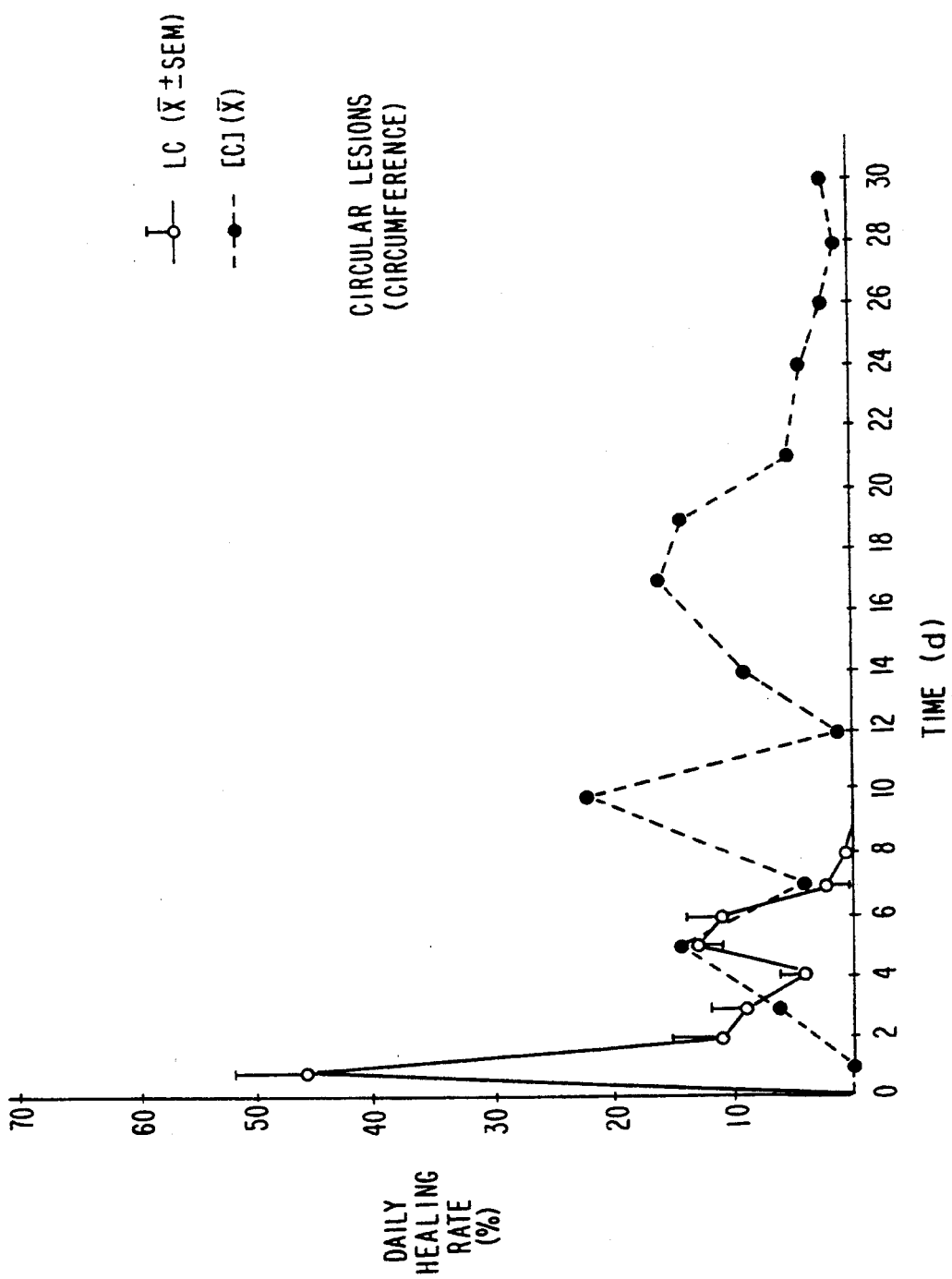
FIG. 10 is a graph depicting the daily rate of change of healing of the circumference of punch biopsy lesions treated with Lumicarmine in an emollient vehicle and circular biopsy lesions in controls without any treatment over time.

Expressed as either cumulative (FIG. 9) or daily (FIG. 10) rate of change in circumference a similar pattern to that observed previously of significantly enhanced wound healing in Lumicarmine treated with respect to untreated control rats was observed, although phase 2 was two days shorter and phase 3 two days longer than in control, untreated rats in whom area was measured.

The results of this study indicate that Lumicarmine treated rats heal wounds significantly faster than do emollient treated or untreated rats. This increased rate over an 11 or 12 day healing period reflects an enhancement of 3–4 days or about 25%. The initial enhancement was observed on Day 1 and varied from 19–23% (mean, 21.7%) and enhancement continued throughout the entire period of the study. Healing of 75% of each lesion was obtained between Days 2–in Lumicarmine treated rats but not until Days 6–7 in the emollient treated rats with no data overlap, again indicating an early enhancement of wound healing in the Lumicarmine treated animals. Complete healing occurred 2–4 days earlier in Lumicarmine treated with respect to control rats.

Comparison of lesions in Lumicarmine treated rats with those in untreated controls indicated an even greater enhancement of healing. Wild type or untreated lesions required more than three times as long to heal as did lesions in Lumicarmine treated rats. Among wild type lesions the first phase of healing required 7 days whereas it was completed in 4 days among Lumicarmine treated rats. Phase 2 healing was completed in 4 days among Lumicarmine rats, and at this time, lesions were completely healed; however, phase 2 healing required an additional 7 days in wild type lesions and completion of healing required an additional 16 days, or a full 19 days after completion of healing in the Lumicarmine treated rats.

Emollient treated rats exhibited a beneficial effect of the emollient treatment compared to wild type lesions. Complete healing occurred in 11–12 days in lesions in emollient treated rats whereas 30 days or a period 2½ times as long was required for the wild type lesion to heal completely. Thus, there appears to be a beneficial effect of vitamin E cream or its constituents on wound healing.

The four phase pattern of healing exhibited during daily changes in healing of wild type lesions corresponds numerically with the four general steps of healing described as the mechanism underlying healing in any wound. While phase and step numbers are numerically similar it is unclear if there is any physiological connection between phases of healing and actual physical change in wound characteristics. However, this four phase pattern of healing was observed in emollient treated but not in Lumicarmine treated rats in which only a two phase process was apparent.

Lumicarmine has been shown to accelerate wound healing within 24 hours of application. This rapid acceleration implies that this protein is active in the initial phase of wound healing and supports the concept that this protein provides the matrix upon which wound healing depends. This also supports the concept that this protein is active in the absence of any specific receptor and this quality is important for its successful utilization in the accelerated healing of chronic wounds.

The foregoing also establishes inhibition of the secretion of Lumicarmine by antibodies directed at endogenous secretion of Lumicarmine by human parotid cells in continuous culture. This demonstrates that human parotid cells not only can be grown in continuous culture but also that they still demonstrate normal cellular function. With this technique, it is now possible to bioengineer production of Lumicarmine in amounts which can be useful for commercial applications.

The use of Lumicarmine to accelerate wound healing has many applications in present medical practice. It can be used topically to speed healing of cuts and lacerations. It can also be used to speed healing in burns, venous stasis ulcers, pressure sores, decubital ulcers and skin ulcers since it provides the physiological matrix upon which healing is initiated. It also may be useful in corneal lesions and in bone repair, again, since it can supply the physiological matrix upon which the regenerative process depends for the normal progression of healing. The absence of this matrix in burns, stasis ulcers and pressure sores is one reason why these lesions heal so poorly. Application of artificial gels or manufactured matrices to these wounds have not provided a physiological base upon which the normal healing process may proceed. Lumicarmine then has been shown to be the physiological substance which can be used by animals to heal these wounds by providing the physiological foundation matrix which may be missing or inhibited in chronic, non-healing or poorly healing lesions.

There is also described herein an antifibrosis agent which, when applied to a lesion in which fibrosis is expected, will inhibit scarring or fibrotic activity. In addition, use of Antilumicarmine as an antitumor promotor depends upon its activities in several systems. Antilumicarmine may inhibit angiogensis. This inhibition is important since the generation of new capillary blood vessels is necessary if a tumor is to expand. The degree of angiogenesis, assessed by microvessels at the margin of a primary tumor, has been shown to be predictive of metastatic disease in breast carcinoma. Antilumicarmine may inhibit cell/matrix interactions through interaction with specific cell-surface or cell-adhesion molecules. Substances such as E-cadherin are known to inhibit invasion into collagen gels and loss of this activity may allow this action to occur more readily. Antilumicarmine may interact with E-cadherin and thereby regulate tumor invasive behavior, and tumor progression.

Antilumicarmine may also inhibit endothelium/tumor cell adhesion interactions. By inhibition of the attachment of circulatory leukocytes through inhibition of the action of calcium-dependent lectins [LEC-CAMs or selectins], endothelial cell leukocyte adhesion molecules (ELAM 1) or other similar molecules may inhibit tumor capacity to metastasize. Antilumicarmine may also regulate tumor invasion by inhibiting cell movement into or out of the tumor matrix. Since several growth factors stimulate cell movement Antilumicarmine may inhibit motility of epithelial cells such as autocrine motility factor, migration stimulating factor or scatter factor thereby inhibiting tumor invasion. By inhibiting cell attachment and motility, Antilumicarmine may play a significant role in modulating and regulating cancer spread and provide a new therapeutic modality as an antitumor promoter.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. A medicinal composition for enhancing the wound process in humans consisting essentially of a therapeutic wound healing enhancing effective amount of the protein Lumicarmine having the following characteristics:

about 80% of the total amino acid residues being proline, glycine, and glutamic acid, about 10% of the total amino acid residues being lysine and arginine, and a pink violet color after gel electrophoresis and staining with Coomassie Brilliant Blue R-250 in a pharmaceutically acceptable vehicle for topical application.

2. The composition of claim 1 wherein the pharmaceutically acceptable vehicle is an oil-based emulsion containing vitamin E.

3. The composition of claim 1 wherein the concentration of Lumicarmine is about 45 mg per gram of vehicle.

4. Method of enhancing the healing of lesions in humans consisting essentially of topical application to the lesion of a therapeutically lesion healing effective amount of the composition of claim 1.

5. The method of claim 4 wherein the pharmaceutically acceptable vehicle is an oil-based emulsion.

* * * * *